US012403191B2

(12) United States Patent
Mundt et al.

(10) Patent No.: US 12,403,191 B2
(45) Date of Patent: Sep. 2, 2025

(54) ATTENUATED IBV WITH EXTENDED CELL CULTURE AND TISSUE TROPISM

(71) Applicant: Boehringer Ingelheim Vetmedica GmbH, Ingelheim Am Rhein (DE)

(72) Inventors: Egbert Siegfried Mundt, Lyons (FR); Annika Kraemer-Kuehl, Seesen (DE); Rosalba De La Mora Quiroz, Guadalajara Jalisco (MX); Jose Francisco Robles Gonzalez, County Nueva Oxtotitlan (MX); Thomas Min Stephan, Hannover (DE)

(73) Assignee: BOEHRINGER INGELHEIM VETMEDICA GMBH, Ingelheim am Rhein (DE)

( * ) Notice: Subject to any disclaimer, the term of this patent is extended or adjusted under 35 U.S.C. 154(b) by 943 days.

(21) Appl. No.: 17/595,119

(22) PCT Filed: May 6, 2020

(86) PCT No.: PCT/EP2020/062563
§ 371 (c)(1),
(2) Date: Nov. 9, 2021

(87) PCT Pub. No.: WO2020/229257
PCT Pub. Date: Nov. 19, 2020

(65) Prior Publication Data
US 2022/0202931 A1 Jun. 30, 2022

(30) Foreign Application Priority Data
May 10, 2019 (EP) .................................... 19173827

(51) Int. Cl.
*A61K 39/215* (2006.01)
*A61P 31/14* (2006.01)
*C12N 5/0735* (2010.01)
*C12N 7/00* (2006.01)
*A61K 39/00* (2006.01)

(52) U.S. Cl.
CPC ............ *A61K 39/215* (2013.01); *A61P 31/14* (2018.01); *C12N 5/0606* (2013.01); *C12N 7/00* (2013.01); *A61K 2039/552* (2013.01); *C12N 2770/20034* (2013.01); *C12N 2770/20062* (2013.01)

(58) Field of Classification Search
None
See application file for complete search history.

(56) References Cited

U.S. PATENT DOCUMENTS 2,909,462 A    10/1959   Warfield

FOREIGN PATENT DOCUMENTS

| CN | 101948812 A | 1/2011 |
| CN | 102574897 A | 7/2012 |
| CN | 104353070 A | 2/2015 |
| CN | 108300704 A | 7/2018 |
| WO | 01/64244 A2 | 9/2001 |
| WO | 2011004146 A1 | 1/2011 |
| WO | 2016012793 A1 | 1/2016 |

OTHER PUBLICATIONS

Ellis et al. Recombinant Infectious Bronchitis Viruses Expressing Chimeric Spike Glycoproteins Induce Partial Protective Immunity against Homologous Challenge despite Limited Replication In Vivo. J Virol., 2018, 92:e01473-18.*
Bijlenga et al. Development and use of the H strain of avian infectious bronchitis virus from the Netherlands as a vaccine: a review 2004. Avian Pathol. 33:550-557.
Callison et al. Development and evaluation of a real-time Taqman RT-PCR assay for the detection of infectious bronchitis virus from infected chickens 2006. Journal of Virological Methods 138:60-65.
Casais et al. Recombinant Avian Infectious Bronchitis Virus Expressing a Heterologous Spike Gene Demonstrates that the Spike Protein is a Determinant of Cell Tropism 2003. J. Virol. 77; 9084-9089.
Cavanagh Coronavirus avian infectious bronchitis virus 2007. Vet. Res. 38:281-297.
Chen et al. Infection of HeLa cells by avian infectious bronchitis virus is dependent on cell status 2007. Avian Pathology 36(4):269-274.
Cook et al. The long view: 40 years of infectious bronchitis research 2012. Avian Pathol. 41:239-250.
Dancey et al. Effect of Liposomal Model Membrane Composition on Immunogenicity 1978, J. Immunol. 120:1109-13.
Ellis et al. Recombinant Infectious Bronchitis Viruses Expressing Chimeric Spike Glycoproteins Induce Partial Protective Immunity against Homologous Challenge despite Limited Replication In Vivo 2018. J. Virol. 92(23):1-18.
Fang et al. Selection of and recombination between minor variants lead to the adaptation of an avian coronavirus to primate cells 2005. Biochemical and Biophysical Research Communication 336:417 to 423.

(Continued)

*Primary Examiner* — Nianxiang Zou
(74) *Attorney, Agent, or Firm* — Shanyun Lu

(57) ABSTRACT

The present invention relates i.a. to an IBV (infectious bronchitis virus) deposited with the BVR of IZSLER under accession number DPS RE RSCIC 16, any descendant IBV thereof and any IBV having all of the identifying characteristics of the deposited IBV. Further, the present invention relates to an immunogenic composition comprising said deposited IBV.

20 Claims, 1 Drawing Sheet

(56) References Cited

OTHER PUBLICATIONS

Farsang et al. Molecular epizootiology of infectious bronchitis virus in Sweden indicating the involvement of a vaccine strain 2002. Avian Pathology 31:229-236.

Geilhausen et al. The Pathofenesis of Virulent and Avirulent Avian Infeetious Bronchitis Virus 1973. Archiv für die gesamte Virusforschung 40:285-290.

Handberg et al. Detection and strain differentiation of infectious bronchitis virus in tracheal tissues from experimentally infected chickens by reverse transcription polymerase chain reaction. Comparison with an immunohistochemical technique 1999. Avian Pathology 28:327-335.

Hodgson et al. Recombinant Infectious Bronchitis Coronavirus Beaudette with the Spike Protein Gene of the Pathogenic M41 Strain Remains Attenuated but Induces Protective Immunity 2004. J Virol 78:13804-13811.

Kuo et al. Retargeting of Coronavirus by Substitution of the Spike Glycoprotein Ectodomain: Crossing the Host Cell Species Barrier 2000. J. Virol. 74:1393-1406.

McDonald et al. An inverse age resistance of chicken kidneys to infectious bronchitis virus 1980. Avian Pathology 9:245-259.

Promkuntod et al. Mapping of the receptor-binding domain and amino acids critical for attachment in the spike protein of avian coronavirus infectious bronchitisvirus 2014. Virology. 448:26-32.

Rauw et al. The positive adjuvant effect of chitosan on antigen-specific cell-mediated immunity after chickens vaccination with live Newcastle disease vaccine 2009. Vet Immunol Immunop 134:249-258.

Todd et al. Development of an adjuvant-active nonionic block copolymer for use in oil-free subunit vaccines formulations 1997. Vaccine 15:564-570.

Wang et al., Intranasal immunization with live attenuated influenza vaccine plus chitosan as an adjuvant protects mice against homologous and heterologous virus challenge 2012. Arch Virol 157:1451-1461.

Zwaagstra et al. Rapid Detection and Identification of Avian Infectious Bronchitis Virus 1992. J. Clin. Microbiol. 30(1):79-84.

Ali, Ahmed, et al. "Safety and efficacy of attenuated classic and variant 2 infectious bronchitis virus candidate vaccines." Poultry science 97.12 (2018): 4238-4244.

Britton, Paul, et al. "Modification of the avian coronavirus infectious bronchitis virus for vaccine development." Bioengineered Bugs 3.2 (2012): 114-119.

\* cited by examiner

ATTENUATED IBV WITH EXTENDED CELL CULTURE AND TISSUE TROPISM

BACKGROUND OF THE INVENTION

Avian coronavirus infectious bronchitis virus (IBV) is the prototype gammacoronavirus of the family Coronaviridae, order Nidovirales. Infectious bronchitis virus infects the upper respiratory epithelium of chickens, causing a respiratory disease, commonly complicated by secondary bacterial pathogens (Cook et al. 2012. Avian Pathol. 41:239-250). Some IBV strains additionally affect the renal tubuli, oviduct and parts of the gastrointestinal tract, leading to pathological lesions and clinical symptoms in these organ systems. The virus has a worldwide presence in both commercial and backyard chicken. Due to its high genomic variability IBV is discriminated in a wide variety of geno-, sero- and protectotypes. IBV is currently regarded as one of the economically most relevant viral pathogens in the poultry industry.

Infectious bronchitis virus is an enveloped virus with a positive sense single-stranded RNA genome of 27.6 kb (Cavanagh 2007. Vet. Res. 38:281-297). The first two-thirds of the viral genome comprise a large coding region (also designated as gene 1), divided into two open reading frames 1a and 1b, which encode for at least 15 nonstructural proteins involved in RNA replication, editing, and transcription. The last one-third of the viral genome codes for structural proteins: the spike protein (S, encoded by gene 2), the envelope protein (E, encoded by gene 3c), the membrane protein (M, encoded by gene 4), and the nucleocapsid protein (N, encoded by gene 6). Proteins S, E and M are part of the viral envelope while protein N forms the ribonucleoprotein core along with the viral RNA. The coronavirus spike protein determines the host species tropism (Kuo et al. 2000. J. Virol. 74:1393-1406). It is a dimeric or trimeric transmembrane protein, which is proteolytically cleaved into two subunits, S1 and S2. The glycosylated S1 domain forms the 'head' of the spike protein and contains the receptor binding domain that interacts with 2,3-linked sialic acids on the host cell surface (Promkuntod et al. 2014. Virology. 448:26-32). The S2 domain is the remaining part of the ectodomain (the 'stalk'), the transmembrane domain and an endodomain located in the cytoplasm.

The to date widely used live-attenuated IBV vaccine strains H52 and H120 were developed in the 1960s in the Netherlands, by serial passaging of a Massachusetts serotype IBV strain in embryonated chicken eggs (Bijlenga et al. 2004; Avian Pathol. 33:550-557). Said vaccine strains also have to be propagated in embroynated chicken eggs for vaccine production. Today, IBV vaccines (both, inactivated and live vaccines) are still propagated in embryonated chicken eggs which is cumbersome and expensive.

The only cell-line adapted IBV described so far is the IBV strain Beaudette, which efficiently replicates in Vero and BHK cells. Casais et al. 2003 (J. Virol. 77; 9084-9089) show that the S protein of Beaudette is the determinant of cell line tropism by generating recombinant IBVs using ectodomain sequences of the Beaudette spike, which were able to transfer this extended cell line tropism to another IBV (M41). Fang et al. 2005 (Biochemical and Biophysical Research Communication 336; pages 417 to 423) disclose that the adaption of Beaudette for propagation in Vero cells resulted in 49 amino acid modifications, 26 located within the spike protein. However, recombinant IBVs with Beaudette spike are not suitable as vaccines. Ellis et al. 2018 (J. Virol. 92(23)) describe that recombinant Beaudette constructs with chimeric spikes with heterologous S1 subunits from M41 or QX in combination with Beaudette spike S2 subunit do not confer sufficient protection against S1 homologous challenges. Also, Beaudette wild type does not provide procection against homologous challenge like other licensed vaccines belonging to the Massachusetts serotype (Hodgson et al 2004: J Virol 78:13804-13811 or Geilhausen et al 1973: Archiv für die gesamte Virusforschung 40: 285-290).

Taken together, providing IBV vaccines having an extended cell or tissue tropism by exchanging the spike protein to a heterologous Beaudette spike protein (recombinant IBV) would not result in IBV vaccines providing sufficient efficacy, and with the Beaudette spike sequence would be limited to protection against a Massachusetts serotype strain challenge and missing cross protection against further genotypes. Further, the IBV of the present invention is not a GMO (genetically modified organism) in contrast to the recombinant IBVs disclosed in the prior art.

Consequently, there is a need for efficient IBV vaccines having an extended cell or tissue tropism for efficient production. Preferably, such new IBV vaccines with extended cell or tissue tropism are non-recombinant vaccines.

DETAILED DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

Composition of Matter

The present invention solves the problems inherent in the prior art and provides a distinct advance in the state of the art.

Generally, the present invention provides an IBV (infectious bronchitis virus) deposited with the BVR of IZSLER under accession number DPS RE RSCIC 16, any descendant IBV thereof or any IBV having all of the identifying characteristics of the IBV deposited under DPS RE RSCIC 16.

Further, the present invention provides an IBV (infectious bronchitis virus) deposited with the BVR of IZSLER under accession number DPS RE RSCIC 16, any attenuated descendant IBV thereof having an extended cell or tissue tropism and being protective against virulent M41 challenge or any attenuated IBV having an extended cell or tissue tropism and being protective against virulent M41 challenge.

Advantageously, the experimental data show that the deposited strain and its decendants have an extended cell or tissue tropism, they are capable to infect and/or replicate in different cell lines and tissue cells. Surprisingly, the deposited strain and its decendants maintain vaccine efficacy until at least several passages, but have an improved safety.

The deposited IBV (IB66HP) strain is deposited at the BVR of IZSLER (Biobank of Veterinary Resources of the Istituto Zooprofilattico Sperimentale della Lombardia edell'Emilia Romagna "Bruno Ubertini" Biobank of Veterinary Resource, Via A Bianchi, 9, 25124 Brescia BS, Italy) under the Budapest Treaty under accession number DPS RE RSCIC 16. The date of the deposit or transfer is 28 Mar. 2019. The deposited microorganism was tested viable.

The term "IBV" refers to the infectious bronchitis virus which is well known to the person skilled in the art. The term "IBV" encompasses all strains, genotypes, protectotypes, and serotypes of infectious bronchitis virus.

The term "being protective against virulent M41 challenge" means that said IBV provides protection against virulent M41 challenge or infection for subjects vaccinated with said IBV.

In one specific aspect of the IBV according to the present invention the IBV is attenuated.

The term "attenuated" refers to a pathogen having a reduced virulence in comparison to the wildtype isolate. In the present invention, an attenuated IBV is one in which the virulence has been reduced so that it does not cause clinical signs of an IBV infection but is capable of inducing an immune response in the target animal, but may also mean that the clinical signs are reduced in incidence or severity in animals infected with the attenuated IBV in comparison with a "control group" of animals infected with non-attenuated IBV and not receiving the attenuated virus. In this context, the term "reduce/reduced" means a reduction of at least 10%, preferably 25%, even more preferably 50%, still more preferably 60%, even more preferably 70%, still more preferably 80%, still more preferably 90%, even more preferably 95% and most preferably of 100% as compared to the control group infected with non-attenuated IBV as defined above. Thus, an attenuated IBV strain is one that is suitable for incorporation into an immunogenic composition comprising a modified live IBV.

In another specific aspect of the IBV according to the present invention the IBV is attenuated in one-day-old chickens.

In another specific aspect of the IBV according to the present invention the IBV is inactivated.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation may also comprise a neutralization step. Preferred neutralization agents include but are not limited to sodium thiosulfate, sodium bisulfite and the alike.

Preferred formalin inactivation conditions include formalin concentration between from about 0,02% (v/v)-2,0% (v/v), more preferably from about 0.1% (v/v)-1,0% (v/v), still more preferably from about 0,15% (v/v)-0,8% (v/v), even more preferably from about 0,16% (v/v)-0,6% (v/v), and most preferably about 0,2% (v/v)-0,4% (v/v). Incubation time depends on the resistance of the IBV. In general, the inaction process is performed until no growth of the IBV can be detected in a suitable cultivation system.

Preferably, the inactivated IBV of the present invention is formalin inactivated, preferably using the concentrations as described hereinabove.

The inactivated IBV of the invention may be incorporated into liposomes using known technology such as that described in Nature, 1974, 252, 252-254 or Journal of Immunology, 1978, 120, 1109-13. In another embodiment of the invention, the inactivated IBV of the invention may be conjugated to suitable biological compounds such as polysaccharides, peptides, proteins, or the like, or a combination thereof.

In another specific aspect of the IBV according to the present invention the IBV is a non-recombinant.

The term "non-recombinant" as used herein relates to a RNA genome (or RNA sequence, cDNA sequence or protein) having no modifications (such as insertions, deletions, inversions, relocations or a point mutations) introduced recombinantly by human intervention. The term "non-recombinant" as used with respect to a virus, means a virus not produced by recombinant artificial manipulation of the viral genome. The term "non-recombinant virus" excludes recombinant genetically modified viruses. The term "genetically engineered" refers to an IBV which has been mutated by using "reverse genetic" approaches where either a viral cDNA or a chemically synthesized RNA was involved.

The term "protein", "amino acid" and "polypeptide" are used interchangeably. The term "protein" refers to a sequence of amino acids composed of the naturally occurring amino acids as well as derivatives thereof. The naturally occurring amino acids are well known in the art and are described in standard text books of biochemistry. Within the amino acid sequence the amino acids are connected by peptide bonds. Further, the two ends of the amino acid sequence are referred to as the carboxyl terminus (C-terminus) and the amino terminus (N-terminus). The term "protein" encompasses essentially purified proteins or protein preparations comprising other proteins in addition. Further, the term also relates to protein fragments. Moreover, it includes chemically modified proteins. Such modifications may be artificial modifications or naturally occurring modifications such as phosphorylation, glycosylation, myristylation and the like.

In another specific aspect of the IBV according to the present invention the IBV is of a Massachusetts genotype or serotype.

IBV strains can be classified by serotype and genotype. Serotype classification involves treatment of the virus with neutralizing antibodies, whereas genotype classification generally involves examining the sequence of the 51 (spike) protein. However, the different IBV strains are well known to the person skilled in the art. Infectious bronchitis virus was first discovered in the United States in the 1930s.

The first IBV serotype identified was Massachusetts and remained the only serotype until the discovery of a different IBV seroptpye in 1956. Today, IBV Mass (Massachusetts) viruses can be identified in many countries of the world.

The IBV strain Beaudette is of Massachusetts type and was derived following at least 150 passages in chick embryos. The IBV strain Beaudette was originally isolated by Beaudette and Hudson (J. Am. Vet. Med. A. 90, 51-60, 1937) and passaged in chicken embryos. Other Massachusetts type IBV strains besides Beaudette are H120, H52, and M41. The H120 strain was passaged 120 times in embryonated chickens eggs.

It is in the general knowledge of a person skilled in the art where to obtain any IBV strains. IBV strains can be be commercially purchased, obtained from scientific institutes or the genomes can be synthesized as complementary DNA as IBV strains have been sequenced and the sequences have been published and are, thus, available. Furthermore, IBV strains can be isolated from samples obtained from infected chickens. The methods to isolate IBV strains and to characterize the IBV strains are well known to the person skilled in the art. Valter Leonardo de Quadros 2011 (Dissertation, Das Infektiöse Bronchitis Virus (IBV): Molekularbiologische Untersuchungen zur Diagnostik and zum Vorkommen sowie zur Pathogenität des Genotyps IBV QX in spezifisch pathogenfreien (SPF) Broilern, Freie Universität Berlin) and Farsang et al. 2002 (Avian Pathology 31: 229-236) describe how to isolate and differentiate different IBV strains.

In another specific aspect of the IBV according to the present invention the IBV is a M41, H52 or H120 strain.

In another specific aspect of the IBV according to the present invention the IBV is a M41 strain.

In another specific aspect of the IBV according to the present invention the IBV is a H52 or H120 strain.

It is in the general knowledge of a person skilled in the art where to obtain IBV M41, H52 or H120. Exemparily, IBV H52 strains can be commercially purchased such as exemplary Nobilis IB H52 (MSD Animal Health), AviPro IB H52 (Lohmann Animal Health GmbH & Co. KG), Bronchovac (Ceva) and the alike. IBV H120 strains can be commercially purchased such as exemplary BIORAL H120 (Boehringer Ingelheim), HatchPak IB H120 (Boehringer Ingelheim), AviPro IB H120 (Lohmann Animal Health GmbH & Co. KG), Poulvac IB H120 (Zoetis) and the alike. IBV M41 strains can be commercially purchased such as exemplary Volvac IB Fit (Boehringer Ingelheim). Further, McDonald et al 1980 (Avain Pathology 9:245-259) disclose that IBV H52 can be obtained by Central Veterinary Laboratory Rotterdam, Kusters (J. gen Virol 68:343-352) disclose that IBV H52 can be obtained by the Poultry Health Institute Dorn in the Netherlands (GD Animal Health) and Chen et al 2007 (Avian Pathology 36(4):269-274) disclose that IBV H52 can be obtained by the China Institute of Veterinary Drug Control. Furthermore, IBV M41, H52 or H120 are used as vaccine strains for decades and, therefore, can be found and isolated from the field. The methods to isolate IBV M41, H52 or H120 strains and to characterize the IBV H52 strains are well known to the person skilled in the art. Exemplary, IBV H52 strains can be characterized as described in Zwaagstra et al 1992 (J. Clin. Microbiol. 30 (1): 79-84), Handberg et al 1999 (Avian Pathology 28: 327-335) or Callison et al 2006 (Journal of Virological Methods 138: 60-65). Zwaagstra et al 1992 and Handberg et al 1999 for example disclose Massachusetts specifc Primers (for the S and N protein, respectively) for RT-PCR and sequencing and reference sequences for comparison. Further, H52 IBVs have been sequenced and the genomic sequences are available such as EU817497. Thus, the virus genome can be generated by synthesizing its sequence and generated upon the application of reverse genetic systems.

Extended Cell or Tissue Tropism

In another specific aspect of the IBV according to the present invention the IBV has an extended cell or tissue tropism.

The term "cell or tissue" is known by the person skilled in the art. The term cell encompasses cell lines such as the cell lines listed elsewhere herein as well as primary cells. The term tissue encompasses cells from tissues such as the ones listed elsewhere herein, exemplarily such as primary chicken embryo cells from lung or liver or primary chicken fibroblasts. Encompassed is the propagation of cells or tissue (cells) in culture outside the organism. The term "culture" relates to the propagation of cells (such as cell line cells or primary cells or tissue cells) outside the organism under defined culture conditions known by the person skilled in the art.

The term "extended tropism" means that the IBV of the invention can be propagated in cells (such as cell lines) or tissue cells (in addition to primary chicken embryo cells from kidney). In contrast, IBV vaccines described in the prior art or non-cell adapted wildtype IBVs (cell adapted IBV Beaudette strains are described) can only be propagated in embryonated chicken eggs or primary chicken embryo cells from kidney (after adaption). Accordingly, an IBV of the invention with extended cell or tissue tropism has the capacity to infect and/or replicate in one or more cell lines or tissue cells other than primary chicken embryo cells from kidney. Preferebly, the IBV of the invention with extended cell or tissue tropism has the capacity to infect and/or replicate in one or more cell lines as listed herein. Accordingly, an IBV with extended cell or tissue tropism may, for example, have the capacity to infect and/or replicate in PBS-12SF or HEK 293T cells.

Advantageously, the experimental data show that the deposited strain and its decendants have an extended cell or tissue tropism, they are capable to infect and replicate in different cell lines and tissue cells.

In another specific aspect of the IBV according to the present invention the IBV is infecting and/or replicating in at least one cell line or cell selected from the list consisting of: primary chicken embryo cells from lung or liver or primary chicken fibroblasts, a chicken embryo fibroblast cell line, a duck embryonic stem cell line, a human embryonic kidney cell line, a baby hamster kidney cell line, an african green monkey kidney cell line, a rabbit kidney cell line, a canine kidney cell line, a chicken liver cell line, a bovine kidney cell line, a porcine kidney cell line and an insect cell line.

In another specific aspect of the IBV according to the present invention the IBV is infecting and/or replicating in at least one cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+ (*Spodoptera frugiperda*).

In another specific aspect of the IBV according to the present invention the IBV is infecting and/or replicating in at least one cell line selected from the list consisting of: DF-1, EB66, PBS-12, PBS-12SF, BHK, HEK 293T, Vero, MA104, MDCK, SF9 and RK13.

All mentioned cell lines are well known to the person skilled in the art and are commercially and/or publicly available. MDCK cells are exemplarily deposited at the American Tissue Culture Collection under accession number ATCC CCL-34 or ATCC CRL-2285. DF-1 cells are exemplarily deposited at the American Tissue Culture Collection under accession number ATCC CRL-12203. PBS-12SF cells are exemplarily deposited at the American Tissue Culture Collection under accession number ATCC PTA-8565 or deposited at RRID under CVCL_1K17. BHK-21 cells are exemplarily deposited at the American Tissue Culture Collection under accession number ATCC CCL-10. HEK 293T cells are exemplarily deposited at the American Tissue Culture Collection under accession number ATCC CRL-3216. Vero cells are exemplarily deposited at the American Tissue Culture Collection under accession number ATCC CCL-81. MA104 and cells are exemplarily deposited at the American Tissue Culture Collection under accession number ATCC CRL-2378. RK13 cells are exemplarily deposited at the American Tissue Culture Collection under accession number ATCC CCL-37. SF9 cells are exemplarily deposited at the American Tissue Culture Collection under accession number ATCC CRL-3357 or ATCC PTA-3099.

Preferably, the IBV is infecting and/or replicating in the EB66, BHK, Vero, MA104, MDCK, SF9 and RK13 cell line.

In another specific aspect of the IBV according to the present invention the primary chicken embryo cell is a fibroblast or a cell derived from liver or lung tissue.

Functional Definition—Protection

In another specific aspect of the IBV according to the present invention the IBV is protective against virulent M41 challenge or infection.

The term "protective" or "protective immunological response" or "protective immunity" is defined elsewhere herein.

In another specific aspect of the IBV according to the present invention the protection against virulent M41 challenge or infection is to be determined by ciliostasis score, reduced respiratory clinical signs, reduced viral RNA load in kidney tissue or reduced virus sheeding.

In another specific aspect of the IBV according to the present invention the attenuation of the IBV is increased compared to an IBV without extended cell or tissue tropism.

The term "increased attenuation" means, that the efficacy parameter (in particular ciliostasis, but also rales, egg drop, kidney lesions, watery diarrhea, weight loss, virus load or viral shedding) is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of the same species immunized with an IBV without extended cell or tissue tropism. It is in the general knowledge of a person skilled in the art how to measure the improvement in the efficacy parameters.

In another specific aspect of the IBV according to the present invention the attenuation of the IBV is increased compared to an IBV M41 without extended cell or tissue tropism.

In another specific aspect of the IBV according to the present invention the attenuation of the IBV is increased upon application in 1-day old chickens compared to an IBV without extended cell or tissue tropism.

In another specific aspect of the IBV according to the present invention the attenuation of the IBV is increased upon application in 1-day old chickens compared to an IBV M41 without extended cell or tissue tropism.

All Identifying Characteristics

In another specific aspect of the IBV according to the present invention all identifying characteristics of the deposited IBV means that said IBV is attenuated, has an extended cell or tissue tropism and is protective against virulent M41 challenge or infection.

In another specific aspect of the IBV according to the present invention all identifying characteristics of the deposited IBV means that the IBV is attenuated, has an extended cell or tissue tropism and the same or similar protection profile as the deposited IBV.

In another specific aspect of the IBV according to the present invention all identifying characteristics of the deposited IBV means that the IBV is attenuated, is infecting and/or replicating in at least one cell line selected from the list consisting of DF-1, EB66, PBS-12, PBS-12SF, BHK, HEK 293T, Vero, MA104 and RK13 and has the same or similar protection profile as the deposited IBV.

In another specific aspect of the IBV according to the present invention all identifying characteristics of the deposited IBV means that the IBV is attenuated, is infecting and/or replicating in at least one cell line selected from the list consisting of DF-1, EB66, PBS-12, PBS-12SF, BHK, HEK 293T, Vero, MA104 and RK13 and is protective against virulent M41 challenge or infection.

Descendant

In another specific aspect of the IBV according to the present invention the descendant comprises up to 15 passages in cell culture of the IBV deposited with the BVR of IZSLER under accession number DPS RE RSCIC 16.

In another specific aspect of the IBV according to the present invention the descendant comprises up to 10 passages in cell culture of the IBV deposited with the BVR of IZSLER under accession number DPS RE RSCIC 16.

In another specific aspect of the IBV according to the present invention the descendant comprises up to 5 passages in cell culture of the IBV deposited with the BVR of IZSLER under accession number DPS RE RSCIC 16.

Advantageously, the experimental data show that the deposited strain, but also its decendants have an extended cell or tissue tropism, they are capable to infect and/or replicate in different cell lines and tissue cells. Surprisingly, the deposited strain and its decendants maintain vaccine efficacy until at least several passages and have an improved safety.

In another specific aspect of the IBV according to the present invention said descendant IBV is attenuated, has an extended cell or tissue tropism and is protective against virulent M41 challenge or infection.

In another specific aspect of the IBV according to the present invention said descendant IBV is attenuated, has an extended cell or tissue tropism and the same or similar protection profile as the deposited IBV.

In another specific aspect of the IBV according to the present invention said descendant IBV is attenuated, is infecting and/or replicating in at least one cell line selected from the list consisting of DF-1, EB66, PBS-12, PBS-12SF, BHK, HEK 293T, Vero, MA104 and RK13 and has the same or similar protection profile as the deposited IBV.

In another specific aspect of the IBV according to the present invention said descendant IBV is attenuated, is infecting and/or replicating in at least one cell line selected from the list consisting of DF-1, EB66, PBS-12, PBS-12SF, BHK, HEK 293T, Vero, MA104 and RK13 and is protective against virulent M41 challenge or infection.

Nucleotide Sequences and Plasmids

Further, the present invention provides a nucleotide sequence encoding the IBV as described herein. Thus, the present invention provides a nucleotide sequence encoding an IBV (infectious bronchitis virus) deposited with the BVR of IZSLER under accession number DPS RE RSCIC 16, any attenuated descendant IBV thereof having an extended cell or tissue tropism and being protective against virulent M41 challenge or any attenuated IBV having an extended cell or tissue tropism and being protective against virulent M41 challenge.

Further, the present invention provides a plasmid comprising a nucleotide sequence encoding the IBV as described herein. Thus, the present invention provides a plasmid comprising a nucleotide sequence encoding an IBV (infectious bronchitis virus) deposited with the BVR of IZSLER under accession number DPS RE RSCIC 16, any attenuated descendant IBV thereof having an extended cell or tissue tropism and being protective against virulent M41 challenge or any attenuated IBV having an extended cell or tissue tropism and being protective against virulent M41 challenge.

The term "nucleic acid" or "nucleic acid sequence" or "nucleotide sequence" refers to polynucleotides including DNA molecules, RNA molecules, cDNA molecules or derivatives. The term encompasses single as well as double stranded polynucleotides. The nucleic acid of the present invention encompasses isolated polynucleotides (i.e. isolated from its natural context) and genetically modified forms. Moreover, comprised are also chemically modified polynucleotides including naturally occurring modified polynucleotides such as glycosylated or methylated polynucleotides or artificially modified ones such as biotinylated polynucleotides. Further, the terms "nucleic acid" and "polynucleotide" are interchangeable and refer to any nucleic acid. The terms "nucleic acid" and "polynucleotide" also specifically include nucleic acids composed of nucleotides with the nucleobases other than the five biologically occurring bases (adenine, guanine, thymine, cytosine and uracil).

The term "plasmid" refers to cytoplasmic DNA that replicates independently of the bacterial chromosome within a bacterial host cell.

Cell

Further, the present invention provides a cell comprising the IBV or plasmid as described herein. The cell can be an eukaryotic or prokaryotic cell.

In another specific aspect of the cell according to the present invention the cell is a cell line or cell selected from the list consisting of: primary chicken embryo cells, a chicken embryo fibroblast cell line, a duck embryonic stem cell line, a human embryonic kidney cell line, a baby hamster kidney cell line, an African green monkey kidney cell line, a rabbit kidney cell line, a canine kidney cell line, a chicken liver cell line, a bovine kidney cell line, a porcine kidney cell line and an insect cell line.

In another specific aspect of the cell according to the present invention the cell is a cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A, SF9, SF21 and SF+(*Spodoptera frugiperda*).

In another specific aspect of the cell according to the present invention the cell is a cell line selected from the list consisting of: DF-1, EB66, PBS-12, PBS-12SF, BHK, HEK 293T, Vero, MA104 and RK13.

In another specific aspect of the cell according to the present invention the primary chicken embryo cell is a fibroblast or a cell derived from liver or lung tissue.

Viral Particle, Immunogenic Composition and Vaccine

Further, the present invention provides a viral particle comprising the IBV as described herein.

Further, the present invention provides an immunogenic composition comprising the IBV as described herein.

Further, the present invention provides a vaccine comprising the IBV as described herein.

Further, the present invention provides a modified live vaccine with an extended cell or tissue tropism comprising the IBV as described herein.

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of a IBV infection. The host is also described as "subject". Preferably, any of the hosts or subjects described or mentioned herein is an avian or poultry.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutically response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

The term "modified live" and "attenuated" are used interchangeable herein.

In another specific aspect of the immunogenic composition or vaccine according to the present invention the immunogenic composition or vaccine comprises a pharmaceutically acceptable carrier.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In another specific aspect of the immunogenic composition or vaccine according to the present invention the pharmaceutically acceptable carrier is phosphate buffered saline.

Preferably, the immunogenic composition further comprises sucrose gelatin stabilizer.

Preferably, the pharmaceutically acceptable carrier is chitosan.

Chitosan is a natural deacetylated polysaccharide from chitin in crustaceans (e.g., shrimp, crab), insects, and other invertebrates. Recently, Rauw et al. 2009 (Vet Immunol Immunop 134:249-258) demonstrated that chitosan enhanced the cellular immune response of live Newcastle disease vaccine and promoted its protective effect. Further, Wang et al., 2012 (Arch Virol (2012) 157:1451-1461) have shown results revealing the potential of chitosan as an adjuvant for use in a live attenuated influenza vaccine.

Preferably, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In some aspects, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge MA), GPI-0100 (Galenica Pharmaceuticals, Inc., Birmingham, AL), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), JohnWiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta GA), SAF-M (Chiron, Emeryville CA), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In another specific aspect of the immunogenic composition or vaccine according to the present invention the immunogenic composition or vaccine is effective in the treatment and/or prophylaxis of clinical signs caused by IBV in a subject of need. The terms "treatment and/or prophylaxis", "clinical signs" and "of need" have been defined elsewhere.

In another specific aspect of the immunogenic composition or vaccine according to the present invention said immunogenic composition or vaccine is formulated for a single-dose administration.

The volume for a single-dose has been defined elsewhere herein.

It has furthermore been shown that one dose of the immunogenic composition of the present invention is effective after the administration of such single dose of such immunogenic composition or vaccine.

In another specific aspect of the immunogenic composition or vaccine according to the present invention the immunogenic composition or vaccine is administered subcutaneously, intramuscularly, oral, in ovo, via spray, via drinking water or by eye drop.

In another specific aspect of the immunogenic composition or vaccine according to the present invention the immunogenic composition or vaccine comprises 1 to 10 $\log_{10} EID_{50}$ per dose of the IBV.

In another specific aspect of the immunogenic composition or vaccine according to the present invention the immunogenic composition or vaccine comprises 2 to 5 $\log_{10} EID_{50}$ per dose of the IBV.

In another specific aspect of the immunogenic composition or vaccine according to the present invention the immunogenic composition or vaccine comprises 2 to 4 $\log_{10} EID_{50}$ per dose of the IBV.

Method for Culture

Further, the present invention provides a method for culturing an IBV in a cell line or tissue cell comprising the use of the IBV as described herein. Thus, the present invention provides a method for culturing an IBV in a cell line or tissue cell comprising the use of the IBV deposited with the BVR of IZSLER under accession number DPS RE RSCIC 16, any attenuated descendant IBV thereof having an extended cell or tissue tropism and being protective against virulent M41 challenge or any attenuated IBV having an extended cell or tissue tropism and being protective against virulent M41 challenge.

In another specific aspect of the method for culturing an IBV in a cell line or tissue cell according to the present invention the IBV is infecting and/or replicating in a cell line or tissue cell as described herein.

In another specific aspect of the method for culturing an IBV in a cell line or tissue cell according to the present invention the cell line or tissue cell is selected from the list consisting of: primary chicken embryo cells, a chicken embryo fibroblast cell line, a duck embryonic stem cell line, a human embryonic kidney cell line, a baby hamster kidney cell line, an African green monkey kidney cell line, a rabbit kidney cell line, a canine kidney cell line, a chicken liver cell line, a bovine kidney cell line, a porcine kidney cell line and an insect cell line.

In another specific aspect of the method for culturing an IBV in a cell line or tissue cell according to the present invention the cell line is selected from the list consisiting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A, SF9, SF21 and SF+(*Spodoptera frugiperda*).

In another specific aspect of the method for culturing an IBV in a cell line or tissue cell according to the present invention the cell line is selected from the list consisting of: DF-1, EB66, PBS-12, PBS-12SF, BHK, HEK 293T, Vero, MA104 and RK13.

Kits

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to subjects, especially poultry. Associated with such container(s) can be a notice in the form prescribed by a governmental agency regulating the manufacture, use or sale of pharmaceuticals or biological products, which notice reflects approval by the agency of manufacture, use or sale for administration.

The present invention provides a kit comprising the IBV or the immunogenic composition or vaccine as described herein.

In one specific aspect of the kit according to the present invention the kit further comprises an instruction letter for the treatment and/or prophylaxis of diseases of avians.

In one specific aspect of the kit according to the present invention the kit further comprises an instruction letter for the treatment and/or prophylaxis of diseases of poultry.

In one specific aspect of the kit according to the present invention the kit further comprises an instruction letter for the treatment and/or prophylaxis of IB.

In one specific aspect of the kit according to the present invention the kit further comprises a dispenser capable of administering a vaccine to said animal.

Method of Treatment

Further, the present invention provides a method for immunizing a subject comprising administering to such subject an immunogenic composition as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular IBV infection in a flock or in the reduction in the severity of clinical signs caused by or associated with the particular IBV infection.

Further, the immunization of a subject in need with the immunogenic compositions as provided herewith, results in preventing infection of a subject by IBV infection. Even more preferably, immunization results in an effective, long-lasting, immunological-response against IBV infection. It will be understood that the said period of time will last more than 1 month, preferably more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects of a flock are effectively immunized.

Preferably, a flock of subjects is envisaged in this context which normally, i.e. without immunization, would develop clinical signs normally caused by or associated with an IBV infection. Whether the subjects of a flock are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given flock are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular IBV.

Further, the present invention provides a method of treating or preventing clinical signs caused by IBV in a subject of need, the method comprises administering to the subject a therapeutically effective amount of an immunogenic composition or vaccine as described herein.

As shown in the Examples, the immunogenic composition or vaccine as provided herein has been proven to be efficacious in treating or preventing clinical signs caused by IBV in a subject.

The term "treating or preventing" refers to the lessening of the incidence of the particular IBV infection in a flock or the reduction in the severity of clinical signs caused by or associated with the particular IBV infection. Thus, the term "treating or preventing" also refers to the reduction of the number of subjects in a flock that become infected with the particular IBV (=lessening of the incidence of the particular IBV infection) or to the reduction of the severity of clinical signs normally associated with or caused by a IBV infection or the reduction of virus shedding after infection with the particular IBV or preventing or lessening egg drop in laying hens after infection with the particular IBV in a group of subjects which subjects have received an effective amount of the immunogenic composition as provided herein in comparison to a group of subjects which subjects have not received such immunogenic composition.

The "treating or preventing" generally involves the administration of an effective amount of the immunogenic composition of the present invention to a subject or flock of subjects in need of or that could benefit from such a treatment/prophylaxis. The term "treatment" refers to the administration of the effective amount of the immunogenic composition once the subject or at least some subjects of the flock is/are already infected with such IBV and wherein such subjects already show some clinical signs caused by or associated with such IBV infection. The term "prophylaxis" refers to the administration of a subject prior to any infection of such subject with IBV or at least where such subject or none of the subjects in a group of subjects do not show any clinical signs caused by or associated with the infection by such IBV. The terms "prophylaxis" and "preventing" are used interchangeable in this application.

The term "an effective amount" as used herein means, but is not limited to an amount of antigen, that elicits or is able to elicit an immune response in a subject. Such effective amount is able to lessen the incidence of the particular IBV infection in a flock or to reduce the severity of clinical signs of the particular IBV infection.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected by the particular IBV.

The term "clinical signs" as used herein refers to signs of infection of a subject from IBV. Examples for such clinical signs include but are not limited to respiratory distress, nephritis, salphingitis, abnormal egg production, ruffled feathers, depression, reduced growth rates and reduced appetite. Signs of respiratory distress encompass respiratory signs including gasping, coughing, sneezing, tracheal rales, nasal and ocular discharge, tracheal lesions and ciliostasis in the trachea. Signs of nephritis encompass kidney lesions and watery diarrhea. Signs of abnormal egg production encompass egg drop, eggs of smaller size, inferior shell, reduced internal egg quality, eggs with thin albumen and ciliostasis in the oviduct. However, the clinical signs also include but are not limited to clinical signs that are directly observable from a live animal. Examples for clinical signs that are directly observable from a live animal include nasal and ocular discharge, coughing, gasping, sneezing, tracheal rales, ruffled feathers, conjunctivitis, weight loss, reduced growth rates, reduced appetite, dehydration, watery diarrhea, lameness, lethargy, wasting and unthriftiness and the like.

Preferably, the clinical signs lessened in incidence or severity in a treated subject compared to subjects that are either not treated or treated with an immunogenic composition that was available prior to the present invention but subsequently infected by the particular IBV refer to a reduction of ciliostasis, a reduction of rales, a reduction of egg drop, a reduction of kidney lesions, a reduction of watery diarrhea, a reduction in weight loss, a lower virus load, a reduced viral shedding, or combinations thereof.

The term "in need" or "of need", as used herein means that the administration/treatment is associated with the boosting or improvement in health or clinical signs or any other positive medicinal effect on health of the subjects which receive the immunogenic composition in accordance with the present invention.

Further, the present invention provides a method of reducing the ciliostasis in a subject of need, in comparison to a subject of a non-immunized control group of the same species, the method comprises administering to the subject a therapeutically effective amount of an immunogenic composition or vaccine as described herein.

As shown in the Examples, the immunogenic composition or vaccine as provided herein has been proven to be efficacious in reducing ciliostasis.

The term "ciliostasis" is well known to the person skilled in that art. The surface of the trachea is covered with specialised epithelial cells, which are lined with numerous, motile, hair-like structures called cilia. The term "ciliostasis" encompasses the reduction or loss of cilia and/or loss or partial loss of ciliary activity (movement). Ciliostasis may be determined by examining the inner lining of the tracheal rings for the movement of the cilia. It is in the general knowledge of a person skilled in the art how to determine the movemnet of the cilia in the trachea.

Preferably, the movement of the cilia is not reduced from day 10 after challenge or infection, more preferably from day 5 after challenge or infection, more preferably from day 4 after challenge or infection, more preferably from day 3 after challenge or infection and most preferably from day 1 or 2 after challenge or infection with the IBV as compared to a subject of a non-immunized control group of the same species.

The term "reduction of ciliostasis" means, that the ciliostasis is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the reduction of the ciliostasis.

Further, the present invention provides a method of reducing the viral RNA load in a subject of need, in comparison to a subject of a non-immunized control group of the same species, the method comprising administering to the subject a therapeutically effective amount of an immunogenic composition or vaccine as described herein.

The term "virus load" or "virus titer" is a measure of the severity of an active viral infection, and can be determined by methods known to the person skilled in the art. The term "viral titre" is a measure of infectious units per volume of a virus preparation. Viral titre is an endpoint in a biological procedure and is defined as the dilution at which a certain proportion of tests carried out in parallel show an effect (Reed and Muench, 1938). The determination can be based on the detection of viral proteins such as by antibody binding to the viral proteins and further detection or, alternatively, by detection of viral RNA by amplification methods such as RT-PCR. Monitoring of virion associated viral RNA in plasma by nucleic acid amplification methods is a widely used parameter to assess the status and progression of retroviral disease, and to evaluate the effectiveness of prophylactic and therapeutic interventions. Exemplary, the virus load or virus titer can be calculated by estimating the live amount of virus in an involved body fluid such as a number of RNA copies per milliliter of blood plasma.

The term "reduction of viral RNA load" means, that the viral RNA load is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the reduction of viral RNA load.

Further, the present invention provides the immunogenic composition or vaccine as described herein for use in a method for immunizing a subject, the method comprises administering to the subject a therapeutically effective amount of said immunogenic composition or vaccine.

Further, the present invention provides the immunogenic composition or vaccine as described herein for use in a method of treating or preventing clinical signs caused by IBV in a subject of need, the method comprises administering to the subject a therapeutically effective amount of said immunogenic composition or vaccine.

Further, the present invention provides the immunogenic composition or vaccine as described herein for use in a method of reducing the ciliostasis in a subject of need, in comparison to a subject of a non-immunized control group of the same species, the method comprises administering to the subject a therapeutically effective amount of said immunogenic composition or vaccine.

Further, the present invention provides the immunogenic composition or vaccine as described herein for use in a method of reducing the viral RNA load in a subject of need, in comparison to a subject of a non-immunized control group of the same species, the method comprising administering to the subject a therapeutically effective amount of an immunogenic composition or vaccine.

In one specific aspect of the method or use according to the present invention said subject is avian.

The term "avian" is well known to the person skilled in the art. The term "avian" encompasses all birds including poultry.

In one specific aspect of the method or use according to the present invention said subject is poultry.

The term "poultry" is well known to the person skilled in the art. The term "poultry" encompasses chickens, turkeys, quails, pheasants, guineafowl, geese, and ducks. Further, the term "chicken" includes broiler, laying hens, and reproductive stocks for both also referred as breeders.

In one specific aspect of the method or use according to the present invention said subject is selected from the list consisting of chicken, turkey, quail, or pheasant.

In one specific aspect of the method or use according to the present invention said subject is chicken.

In one specific aspect of the method or use according to the present invention the immunogenic composition or vaccine is administered once.

It is understood, that a single-dose is administered only once. As shown in the Examples the immunogenic composition as provided herein has been proven to be efficacious after the administration of a single dose to a subject of need.

The dose volume per poultry depends on the route of vaccination and the age of the poultry.

Typically, eye drop vaccines are administered in a volume of 1 to 100 µl per dose at any age. Preferably, the single-dose for eye drop vaccines has a total volume between about 5 µl and 70 µl and more preferably between about 20 µl and 50 µl with a single 20 µl, 25 µl, 30 µl, 35 µl, 40 µl, 45 µl or 50 µl dose being preferred. Most preferred, the single-dose for eye drop vaccines has a total volume between between about 30 µl and 50 µl with a single 30 µl, 35 µl, 40 µl, 45 µl or 50 µl dose being preferred.

Spray vaccines may contain the dose in a volume of 25 to 1000 µl for day-old poultry. Preferably, the single-dose for spray vaccines has a total volume between about 50 µl and 5000 µl, more preferably between about 75 µl and 2000 µl, more preferably between about 100 µl and 1000 µl, even more preferably between about 200 µl and 900 µl, even more preferably between about 300 µl and 800 µl and even more preferably between about 400 µl and 700 µl with a single 400 µl, 425 µl, 450 µl, 475 µl, 500 µl, 525 µl, 550 µl, 575 µl, 600 µl, 625 µl, 650 µl, 675 µl or 700 µl dose being preferred. Most preferred the single-dose has a total volume of 400 µl, 450 µl 500 µl, 550 µl, 600 µl, 650 µl or 700 µl.

The vaccine for in ovo vaccination may contain the dose in a volume of 50 to 100 µl, preferably 50 µl. Preferably, the single-dose for in ovo vaccines has a total volume between about 10 µl and 250 µl, more preferably between about 15 µl and 200 µl, even more preferably between about 20 µl and 150 µl, even more preferably between about 30 µl and 100 µl, even more preferably between about 30 µl and 75 µl and with a single 30 µl, 35 µl, 40 µl, 45 µl, 50 µl, 55 µl, 60 µl, 65 µl, 70 µl or 75 µl dose being preferred. Most preferred the single-dose has a total volume of 40 µl, 45 µl, 50 µl, 55 µl or 60 µl.

The vaccine for intramuscular or subcutaneous vaccination or one dose of a drinking water vaccine may contain the dose in a volume of 30 µl to 1000 µl. Preferably, the single-dose has a total volume between about 30 µl and 1000 µl, more preferably between about 50 µl and 500 µl, more preferably between about 75 µl and 250 µl and even more preferably between about 100 µl and 200 µl with a single 100 µl, 110 µl, 120 µl, 125 µl, 130 µl, 135 µl, 140 µl, 145 µl, 150 µl, 160 µl, 170 µl, 175 µl, 180 µl, 190 µl, 155 µl, or 200 µl dose being the most preferred.

In one specific aspect of the method or use according to the present invention the immunogenic composition or vaccine is administered at two or more doses.

However, the immunogenic composition can be administered at two or more doses, with a first dose being administered prior to the administration of a second (booster) dose.

In a preferred aspect of the two-time administration regimen, both the first and second doses of the immunogenic composition are administered in the same amount. Preferably, each dose is in the preferred amounts specified above. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

Preferably, the first administration of the vaccine is performed within the first three weeks of age, more preferably within the first week of age and most preferred at one day-of-age by methods as described below. A second administration can be performed within the first 20 weeks of age, preferably within 16-18 weeks of age, more preferably between 6-12 weeks of age. Exemplary, the iniatial (first) vaccination is performed at 1-10 days of age and the second vaccination (booster) is performed with a live or inactivated vaccine at 6-12 or 16-18 weeks of age. More preferably, the iniatial (first) vaccination is performed at one day-of-age and the second vaccination (booster) is performed with a live or inactivated vaccine at 6-12 or 16-18 weeks of age.

In case in ovo vaccination is used, preferably the first admistration is performed when embryos are between 15 to 19 days old, preferably at day 17, 18 or 19, most preferably at day 18 of age. A second administration can be performed within the first three weeks of age, preferably within the first 10 days of age.

In one specific aspect of the method or use according to the present invention said immunogenic composition or vaccine is administered subcutaneously, intramuscularly, oral, in ovo, via spray, via drinking water or by eye drop.

The immunogenic composition is, preferably, administered topically or systemically. Suitable routes of administration conventionally used are oral or parenteral administration, such as intranasal, intravenous, intradermal, transdermal, intramuscular, intraperitoneal, subcutaneous, as well as inhalation, in ovo, via spray, via drinking water or by eye drop. However, depending on the nature and mode of action of a compound, the immunogenic composition may be administered by other routes as well. For example, such other routes include intracutaneously, intravenously, intravascularly, intraarterially, intraperitnoeally, intrathecally, intratracheally, intracutaneously, intracardially, intralobally, intralobarly, intramedullarly, intrapulmonarily, intrarectally, and intravaginally. However, most preferred the immunogenic composition is administered subcutaneously, intramuscularly, oral, in ovo, via spray, via drinking water or by eye drop.

Live IBV vaccines are preferably administered individually by eye drop, intranasal, intramuscular or subcutaneous.

More preferably, mass application methods, including drinking water and aerosol spray vaccination, are used. Also preferred is the use of vaccines as embryo vaccines (so-called in ovo vaccines) as described further below.

For example, broilers may be vaccinated at one-day of age or at 1-3 weeks of age, particularly for broilers with high levels of MDA. Laying stock or reproduction stock may be vaccinated initially at 1-10 days of age and boosted with the vaccine at 7-12 or 16-18 weeks of age.

As outlined above, the present invention also provides an IBV vaccine that can be safely administered via the in ovo route and at the same time is able to induce a protective immune response. The in ovo administration is well known to the person skilled in the art and the person skilled in the art can perform in ovo administration without further ado. The in ovo administration of the vaccine involves the administration of the vaccine to an avian embryo while contained in the egg (for a review on in ovo vaccination see: Ricks et al., Advances in Vet. Med. 495-515, 1999). The vaccine may be administered to any suitable compartment of the egg (e. g. allantois fluid, yolk sac, amnion, air cell or into the embryo) as described in the art (Sharma; Am. J. Vet. Res. 45 1619-1623, 1984). Preferably the vaccine is administered below the shell (aircell) membrane and chorioallantoic membrane.

Preferably, the vaccine is injected into embryonated eggs during late stages of the embryonation, generally during the final quarter of the incubation period, preferably 3-4 days prior to hatch. Preferably, the admistration is performed when embryos are between 15 to 19 days old, preferably at day 17, 18 or 19, most preferably at day 18 of age. Subsequently, the vaccinated embryonated eggs are transferred to an incubator for hatch. The process of in ovo administration can be automated using a robotic injection process as described in the prior art.

Usually conventional vaccines for post-hatch vaccination of poultry cannot be used for in ovo vaccination, because late stage embryos are highly susceptible to infection with most vaccine viruses examined. However, International patent application WO 01/64244 discloses that IBV vaccines can be used for in ovo administration provided it is applied at a very low doses. Further, Wakenell et al. 1986 (Am. J. Vet. Res., 47 933-938) discloses that passaging an IB vaccine virus in tissue culture rendered the virus apathogenic for embryos.

In one specific aspect of the method or use according to the present invention said immunogenic composition or vaccine is administered via eye drop.

Typically, the live vaccine for post-hatch administration comprises the attenuated IBV in a concentration of $10^1$ to $10^8$ $EID_{50}$ (50% Egg Infective Dose) per dose, preferably in a concentration of $10^2$ to $10^5$ $EID_{50}$ per dose and, more preferably, in a concentration of $10^2$ to $10^4$ $EID_{50}$ per unit dose and, even more preferably, in a concentration of $10^2$ to $10^3$ $EID_{50}$ per dose.

The live vaccine for in ovo administration typically comprises an amount of the attenuated IBV of $10^2$ to $10^7$ $EID_{50}$/embryo, preferably $10^2$ to $10^3$ $EID_{50}$/embryo in a volume of 50 to 100 µl, preferably 50 µl.

Preferably, the immunogenic composition of the present invention comprises the IBV of the present invention in amounts of about 1 to about 10 $\log_{10}$ EID (egg infective dose)$_{50}$/ml per dose, preferably about 2 to about 8 $\log_{10}$ $EID_{50}$ per dose, preferably in an amount of about 2 to about 7 $\log_{10}$ $EID_{50}$ per dose, more preferably in an amount of about 2 to about 6 $\log_{10}$ $EID_{50}$ per dose, even more preferably in an amount of about 2 to about 5 $\log_{10}$ $EID_{50}$ per dose, even more preferably in an amount of about 2 to about 4 $\log_{10}$ $EID_{50}$ per dose, most preferably in an amount of about 2 to about 3 $\log_{10}$ $EID_{50}$ per dose. More preferably, the immunogenic composition of the present invention comprises the IBV of the present invention in amounts of about 1, 1.5, 2, 2.5, 3, 3.5, 4, 4.5, 5, 5.5, 6, 6.5, 7, 7.5 or $\log_{10}$ $EID_{50}$ per dose.

In one specific aspect of the method or use according to the present invention the immunogenic composition or vaccine comprises 1 to 10 $\log_{10}$ $EID_{50}$ per dose of the IBV.

In one specific aspect of the method or use according to the present invention the immunogenic composition or vaccine comprises 2 to 5 $\log_{10}$ $EID_{50}$ per dose of the IBV.

In one specific aspect of the method or use according to the present invention the immunogenic composition or vaccine comprises 2 to 4 $\log_{10}$ $EID_{50}$ per dose of the IBV.

In one specific aspect of the method or use according to the present invention the immunogenic composition or vaccine is administered to subjects within the first week of age, within the first three days of age, within the first two days of age, or within the first day of age.

Preferably, the subject to be immunized is 1, 2, 3, 4, 5, 6, 7, 8, 9, 10, 11, 12, 13, 14, 15, 16, 17, 18, 19, 20 or 21 days of age. More preferably, said subject to be immunized is 1, 2, 3, 4, 5, 6, 7, 8, 9, 10, 11, 12, 13 or 14 days of age. Most preferably, said subject to be immunized is 1, 2, 3, 4, 5, 6 or 7 days of age.

However, it has to be understood that after vaccination of the subject being a few days of age, it does need several days for the immune system of the poultry to build up immunity against an IBV infection. Therefore, preferably, the subjects are immunized within the first 24 h of age.

In one specific aspect of the method or use according to the present invention the immunogenic composition or vaccine is administered to subjects within the first day of age. As shown in the Examples the immunogenic composition as provided herein has been proven to be safe and efficacious when administered to 1-day old poultry.

In one specific aspect of the method or use according to the present invention said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

The terms "treatment and/or prophylaxis" have been defined elsewhere, wherein the terms "prophylaxis" and "preventing" or "prevention" are used interchangeable in this application. Further, the terms "shedding" has been defined elsewhere, too.

The term "reducing", "reduced", "reduction" or "lower" means, that the efficacy parameter (ciliostasis, rales, egg drop, kidney lesions, watery diarrhea, weight loss, virus load, viral shedding) is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the improvement in the efficacy parameters.

The term "virus load" has been defined elsewhere herein.

The term "ciliostasis" has been defined elsewhere herein.

The term "rales" is well known to the person skilled in that art. However, the term "rales" encompasses tracheal rales and refers to sounds emanating from the bronchi. Rales can be determined without further ado by the person skilled in the art.

The term "egg drop" is well known to the person skilled in that art. The term "egg drop" encompasses a decreased egg production.

In one specific aspect of the method or use according to the present invention the treatment or prevention results in a prevention or reduction of ciliostasis as compared to subjects of a non-treated control group of the same species.

In one specific aspect of the method or use according to the present invention the treatment or prevention results in a prevention or reduction of kidney lesions as compared to subjects of a non-treated control group of the same species.

In one specific aspect of the method or use according to the present invention the treatment or prevention results in a prevention or reduction of egg drop as compared to subjects of a non-treated control group of the same species.

The present invention further provides the IBV, the viral particle or the immunogenic composition or vaccine as described herein for therapeutic use.

The present invention further provides the IBV or the viral particle as described herein for use as an immunogen or vaccine.

The present invention further provides the IBV, the viral particle or the immunogenic composition or vaccine as described herein for use as a medicament.

The present invention further provides the use of the IBV, the viral particle or the immunogenic composition or vaccine as described herein for the manufacture of a medicament.

The present invention further provides the use of the IBV, the viral particle or the immunogenic composition or vaccine as described herein for the treatment and/or prophylaxis of IBV infections in a subject.

In another specific aspect of the IBV according to the present invention the IBV is phenotypically stable. Advantageously, the experimental data show that the deposited strain and its decendants are phenotypically stable since the extended cell culture/tissue tropism and attenuation remains stable over time (over passage).

The term "phenotypically stable" means that the IBV remains its functional features of having an extended cell culture/tissue tropism and being attenuated over time (over passage). Preferably, said functional features are still present after at least 3 passages, more preferably after at least 6 passages, even more preferably after at least 9 passages, even more preferably after at least 12 passages, most preferred after 15 passages of the IBV in cell culture or tissue culture.

CLAUSES

The following clauses are also described herein:

1. An IBV (infectious bronchitis virus) deposited with the BVR of IZSLER under accession number DPS RE RSCIC 16, any descendant IBV thereof or any IBV having all of the identifying characteristics of the IBV deposited under DPS RE RSCIC 16.

2. An IBV (infectious bronchitis virus) deposited with the BVR of IZSLER under accession number DPS RE RSCIC 16, any attenuated descendant IBV thereof having an extended cell or tissue tropism and being protective against virulent M41 challenge or any attenuated IBV having an extended cell or tissue tropism and being protective against virulent M41 challenge.

3. The IBV of clause 1 or 2, wherein the IBV is attenuated.

4. The IBV of any one of clauses 1 to 3, wherein the IBV is attenuated in one-day-old chickens.

5. The IBV of any one of clauses 1 to 4, wherein the IBV is non-recombinant.

6. The IBV of any one of clauses 1 or 5, wherein the IBV is of a Massachusetts genotype or serotype.

7. The IBV of any one of clauses 1 or 6, wherein the IBV is a M41, H52 or H120 strain.

Extended Cell or Tissue Tropism

8. The IBV of any one of clauses 1 or 7, wherein the IBV has an extended cell or tissue tropism.

9. The IBV of any one of clauses 1 to 8, wherein the IBV is infecting and/or replicating in a cell line or cell selected from the list consisiting of: primary chicken embryo cells from lung or liver or primary chicken fibroblasts, a chicken embryo fibroblast cell line, a duck embryonic stem cell line, a human embryonic kidney cell line, a baby hamster kidney cell line, an african green monkey kidney cell line, a rabbit kidney cell line, a canine kidney cell line, a chicken liver cell line, a bovine kidney cell line, a porcine kidney cell line and an insect cell line.

10. The IBV of any one of clauses 1 to 9, wherein the IBV is infecting and/or replicating in at least one cell line selected from the list consisting of: DF-1 (Douglas Foster), EB66

(duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A, SF9, SF21 and SF+(*Spodoptera frugiperda*).

11. The IBV of any one of clause 1 to 10, wherein the IBV is infecting and/or replicating in at least one cell line selected from the list consisting of: DF-1, EB66, PBS-12, PBS-12SF, BHK, HEK 293T, Vero, MA104, MDCK, SF9 and RK13.

12. The IBV of clause 9, wherein the primary chicken embryo cell is a fibroblast or a cell derived from liver or lung tissue.

Functional Definition—Protection

13. The IBV of any one of clauses 1 to 12, wherein the IBV is protective against virulent M41 challenge or infection.

14. The IBV of clause 13, wherein the protection against virulent M41 challenge or infection is to be determined by ciliostasis score, reduced respiratory clinical signs, reduced viral RNA load in kidney tissue or reduced virus sheeding.

15. The IBV of any one of clauses 1 to 14, wherein the attenuation of the IBV is increased compared to an IBV without extended cell or tissue tropism.

16. The IBV of any one of clauses 1 to 15, wherein the attenuation of the IBV is increased compared to an IBV M41 without extended cell or tissue tropism.

17. The IBV of any one of clauses 1 to 16, wherein the attenuation of the IBV is increased upon application in 1-day old chickens compared to an IBV without extended cell or tissue tropism.

18. The IBV of any one of clauses 1 to 17, wherein the attenuation of the IBV is increased upon application in 1-day old chickens compared to an IBV M41 without extended cell or tissue tropism.

All Identifying Characteristics

19. The IBV of any one of clauses 1 to 18, wherein all identifying characteristics of the deposited IBV means that said IBV is attenuated, has an extended cell or tissue tropism and is protective against virulent M41 challenge or infection.

20. The IBV of any one of clauses 1 to 19, wherein all identifying characteristics of the deposited IBV means that the IBV is attenuated, has an extended cell or tissue tropism and the same or similar protection profile as the deposited IBV.

21. The IBV of any one of clauses 1 to 20, wherein all identifying characteristics of the deposited IBV means that the IBV is attenuated, is infecting and/or replicating in at least one cell line selected from the list consisting of DF-1, EB66, PBS-12, PBS-12SF, BHK, HEK 293T, Vero, MA104 and RK13 and has the same or similar protection profile as the deposited IBV.

22. The IBV of any one of clauses 1 to 21, wherein all identifying characteristics of the deposited IBV means that the IBV is attenuated, is infecting and/or replicating in at least one cell line selected from the list consisting of DF-1, EB66, PBS-12, PBS-12SF, BHK, HEK 293T, Vero, MA104 and RK13 and is protective against virulent M41 challenge or infection.

Descendant

23. The IBV of any one of clauses 1 to 22, wherein said descendant IBV is attenuated, has an extended cell or tissue tropism and is protective against virulent M41 challenge or infection.

24. The IBV of any one of clauses 1 to 23, wherein said descendant IBV is attenuated, has an extended cell or tissue tropism and the same or similar protection profile as the deposited IBV.

25. The IBV of any one of clauses 1 to 24, wherein said descendant IBV is attenuated, is infecting and/or replicating in at least one cell line selected from the list consisting of DF-1, EB66, PBS-12, PBS-12SF, BHK, HEK 293T, Vero, MA104 and RK13 and has the same or similar protection profile as the deposited IBV.

26. The IBV of any one of clauses 1 to 25, wherein said descendant IBV is attenuated, is infecting and/or replicating in at least one cell line selected from the list consisting of DF-1, EB66, PBS-12, PBS-12SF, BHK, HEK 293T, Vero, MA104 and RK13 and is protective against virulent M41 challenge or infection.

27. A plasmid comprising a nucleotide sequence encoding the IBV of any one of clauses 1 to 26.

28. A cell comprising the IBV or plasmid of any one of clauses 1 to 27.

29. The cell according to clause 28, wherein the cell is a cell line or cell selected from the list consisting of: primary chicken embryo cells, a chicken embryo fibroblast cell line, a duck embryonic stem cell line, a human embryonic kidney cell line, a baby hamster kidney cell line, an African green monkey kidney cell line, a rabbit kidney cell line, a canine kidney cell line, a chicken liver cell line, a bovine kidney cell line, a porcine kidney cell line and an insect cell line.

30. The cell according to clauses 28 or 29, wherein the cell is a cell line selected from the list consisiting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A, SF9, SF21 and SF+(*Spodoptera frugiperda*).

31. The cell of any one of clauses 28 to 30, wherein the cell is a cell line selected from the list consisting of: DF-1, EB66, PBS-12SF, BHK, HEK 293T, Vero, MA104 and RK13.

32. The cell of clause 29, wherein the primary chicken embryo cell is a fibroblast or a cell derived from liver or lung tissue.

33. A viral particle comprising the IBV of any one of clauses 1 to 26.

34. An immunogenic composition comprising the IBV of any one of clauses 1 to 26.

35. A vaccine comprising the IBV of any one of clauses 1 to 26.

36. A modified live vaccine with an extended cell or tissue tropism comprising the IBV of any one of clauses 1 to 26.

37. The immunogenic composition or vaccine of any one of clauses 34 to 36, wherein the immunogenic composition or vaccine comprises a pharmaceutically acceptable carrier.

38. The immunogenic composition or vaccine of clause 37, wherein the pharmaceutically acceptable carrier is phosphate buffered saline.

39. The immunogenic composition or vaccine of any one of clauses 34 to 38, wherein the immunogenic composition or vaccine is effective in the treatment and/or prophylaxis of clinical signs caused by IBV in a subject of need.

40. The immunogenic composition or vaccine of any one of clauses 34 to 39, wherein the immunogenic composition or vaccine comprises 1 to 10 $\log_{10}$ $EID_{50}$ of the IBV per dose.

41. The immunogenic composition or vaccine of any one of clauses 34 to 40, wherein the immunogenic composition or vaccine comprises 2 to 5 $\log_{10}$ $EID_{50}$ of the IBV per dose.

42. The immunogenic composition or vaccine of any one of clauses 34 to 41, wherein the immunogenic composition or vaccine comprises 2 to 4 $\log_{10}$ $EID_{50}$ of the IBV per dose.

43. A kit comprising the IBV of any one of clauses 1 to 26 or the immunogenic composition or vaccine of any one of clauses 34 to 42.

44. The kit according to clause 43, wherein the kit further comprises an instruction letter for the treatment and/or prophylaxis of diseases of avians.

45. The kit according to clause 43, wherein the kit further comprises an instruction letter for the treatment and/or prophylaxis of diseases of poultry.

46. The kit according to clauses 43, wherein the kit further comprises an instruction letter for the treatment and/or prophylaxis of IB.

47. A method for immunizing a subject comprising administering to such subject an immunogenic composition or vaccine according to any one of clauses 34 to 42.

48. A method of treating or preventing clinical signs caused by IBV in a subject of need, the method comprising administering to the subject a therapeutically effective amount of an immunogenic composition or vaccine according to any one of clauses 34 to 42.

49. A method of reducing the ciliostasis in a subject of need, in comparison to a subject of a non-immunized control group of the same species, the method comprising administering to the subject a therapeutically effective amount of an immunogenic composition or vaccine according to any one of clauses 34 to 42.

50. A method of reducing the viral RNA load in a subject of need, in comparison to a subject of a non-immunized control group of the same species, the method comprising administering to the subject a therapeutically effective amount of an immunogenic composition or vaccine according to any one of clauses 34 to 42.

51. The immunogenic composition or vaccine according to any one of clauses 34 to 42 for use in a method for immunizing a subject, the method comprising administering to the subject a therapeutically effective amount of said immunogenic composition or vaccine.

52. The immunogenic composition or vaccine according to any one of clauses 34 to 42 for use in a method of treating or preventing clinical signs caused by IBV in a subject of need, the method comprising administering to the subject a therapeutically effective amount of said immunogenic composition or vaccine.

53. The immunogenic composition or vaccine according to any one of clauses 34 to 42 for use in a method of reducing the ciliostasis in a subject of need, in comparison to a subject of a non-immunized control group of the same species, the method comprising administering to the subject a therapeutically effective amount of said immunogenic composition or vaccine.

54. The immunogenic composition or vaccine according to any one of clauses 34 to 42 for use in a method of reducing the viral RNA load in a subject of need, in comparison to a subject of a non-immunized control group of the same species, the method comprising administering to the subject a therapeutically effective amount of said immunogenic composition or vaccine.

55. The method or use of any one of clauses 47 to 54, wherein said subject is avian.

56. The method or use of any one of clauses 47 to 55, wherein said subject is poultry.

57. The method or use of any one of clauses 47 to 56, wherein said subject is selected from the list consisting of chicken, turkey, quail, or pheasant.

58. The method or use of any one of clauses 47 to 57, wherein said subject is chicken.

59. The method or use of any one of clauses 47 to 58, wherein the immunogenic composition or vaccine is administered once.

60. The method or use of any one of clauses 47 to 58, wherein the immunogenic composition or vaccine is administered at two or more doses.

61. The method or use of any one of clauses 47 to 60, wherein said immunogenic composition or vaccine is administered subcutaneously, intramuscularly, oral, in ovo, via spray, via drinking water or by eye drop.

62. The method or use of any one of clauses 47 to 61, wherein said immunogenic composition or vaccine is administered via eye drop.

63. The method or use of any one of clauses 47 to 62, wherein the immunogenic composition or vaccine comprises 1 to 10 $\log_{10}$ $EID_{50}$ per dose of the IBV.

64. The method or use of any one of clauses 47 to 63, wherein the immunogenic composition or vaccine comprises 2 to 5 $\log_{10}$ $EID_{50}$ per dose of the IBV.

65. The method or use of any one of clauses 47 to 64, wherein the immunogenic composition or vaccine comprises 2 to 4 $\log_{10}$ $EID_{50}$ per dose of the IBV.

66. The method or use of any one of clauses 47 to 65, wherein the immunogenic composition or vaccine is administered to subjects within the first week of age, within the first three days of age, within the first two days of age, or within the first day of age.

67. The method or use of any one of clauses 47 to 66, wherein the immunogenic composition or vaccine is administered to subjects within the first day of age.

68. The method or use of any one of clauses 47 to 67, wherein said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

69. The method or use of any one of clauses 47 to 68, wherein the treatment or prevention results in a prevention or reduction of ciliostasis as compared to subjects of a non-treated control group of the same species.

70. The method or use of any one of clauses 47 to 69, wherein the treatment or prevention results in a prevention or reduction of kidney lesions as compared to subjects of a non-treated control group of the same species.

71. The method or use of any one of clauses 47 to 70, wherein the treatment or prevention results in a prevention or reduction of egg drop as compared to subjects of a non-treated control group of the same species.

72. The IBV of any one of clauses 1 to 26, the viral particle of clause 33 or the immunogenic composition or vaccine of any one of clauses 34 to 42 for therapeutic use.

73. The IBV of any one of clauses 1 to 26 or the viral particle of clause 33 for use as an immunogen or vaccine.

74. The IBV of any one of clauses 1 to 26, the viral particle of clause 33 or the immunogenic composition or vaccine of any one of clauses 34 to 42 for use as a medicament.

75. Use of the IBV of any one of clauses 1 to 26, the viral particle of clause 33 or the immunogenic composition or vaccine of any one of clauses 34 to 42 for the manufacture of a medicament.

76. Use of the IBV of any one of clauses 1 to 26, the viral particle of clause 33 or the immunogenic composition or vaccine of any one of clauses 34 to 42 for the treatment and/or prophylaxis of IBV infections in a subject.

77. The IBV of any one of clauses 1 to 26, wherein the descendant comprises up to 15 passages in cell culture of the IBV deposited with the BVR of IZSLER under accession number DPS RE RSCIC 16.

78. The IBV of any one of clauses 1 to 26, wherein the descendant comprises up to 10 passages in cell culture of the IBV deposited with the BVR of IZSLER under accession number DPS RE RSCIC 16.

79. The IBV of any one of clauses 1 to 26, wherein the descendant comprises up to 5 passages in cell culture of the IBV deposited with the BVR of IZSLER under accession number DPS RE RSCIC 16.

80. The IBV of any one of clauses 1 to 26 or 77 to 79, wherein the IBV is phenotypically stable.

EXAMPLES

The following examples are set forth below to illustrate specific embodiments of the present invention. These examples are merely illustrative and are understood not to limit the scope or the underlying principles of the present invention.

Example 1

Adaption of IBV to Cells and In Vitro and In Vivo Characterization

Figure 1:
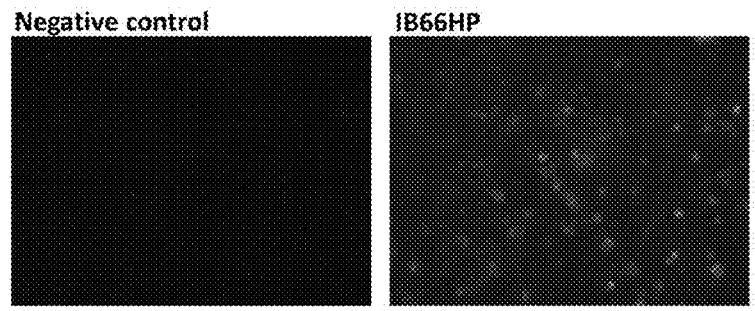
FIG. 1.: Immunofluorescence staining for IB66HP-infected EB66® cells.

An attenuated IBV M41 is used for 10 serial passages in EB66® cells. The material harvested after each passage is characterized by $EID_{50}$ and $TCID_{50}$. Indeed, infective titers are detected already in the first passage after inoculation of EB66® cells with an attenuated IBV Mass seed stock. Results for $EID_{50}$ (infectivity for embryonated eggs) and $TCID_{50}$ (infectivity for cell culture) titer determination for the first 10 passages and are summarized in table 1 and detection of immunofluorescence signal for IB66HP infected EB66® cells in FIG. 1. The results confirm that the IBV is adapted to cell culture in EB66® cells. The IBV is efficiently adapted after one passage in EB66® cells, whereas the infectivity for embryonated eggs is not affected. A passage 4 of the IBV (IB66HP) is deposited at the BVR of IZSLER (Biobanking of Veterinary Resources of the Istituto Zooprofilattico Sperimentale della Lombardia e dell'Emilia Romagna "Bruno Ubertini") under accession number DPS RE RSCIC 16.

TABLE 1

Summary of $EID_{50}$ and $TCID_{50}$ titers throughout IB66HP passaging in EB66 ® cells.

| Passage | 1 | 2 | 3 | 4 | 5 | 6 | 7 | 8 | 9 | 10 |
|---|---|---|---|---|---|---|---|---|---|---|
| $EID_{50}$/ml | 5.6 | 9 | 7.1 | 5.3 | 7 | 7 | 6.8 | 7.5 | 6.6 | 6.6 |
| $TCID_{50}$/ml | 1 | 6.5 | 4.25 | 5.5 | 6.3 | 6.32 | 4.6 | 7 | 6 | 5.4 |

From table 1 and the other experiments further below, it is appearent that IB66 HP is phenotypically stable since the extended cell culture/tissue tropism and attenuation remains over time (over passage).

Serial Passaging in EB66® Cells

EB66® cells are seeded at a density of $10^6$ cells/ml into a 250 ml shaker flask with a total volume of 50 ml in GRO I medium (SIGMA, cat.: 141530C) supplemented with glutamine and 1 ml CHO feed (SIGMA, cat: 1615). The cells are infected with a 1/10 dilution of attenuated IBV Mass seed stock for the first passage which is incubated for 96 hours. For the following passages 2 to 10 inoculation with the harvested culture is performed with a 1/10 dilution of the previous passage into freshly seeded EB66® cells which are subsequently incubated for 48 to 96 hours under the same cultivation conditions. A passage 4 (supernatant) was generated for deposit by inoculation of $4*10^5$ cells/ml with a 1/250 dilution of passage 3 and was harvested 72 hours post infection and he titer of the harvested material is determined by the 50% embryo infectious dose ($EID_{50}$) and immunofluorescence tissue culture infectious dose 50 ($TCID_{50}$) assay which are $10^{5.75}$/ml and $10^{7.33}$/ml, respectively.

Determination of the 50% Embryo Infectious Dose ($EID_{50}$)

For the determination of the $EID_{50}$ titer 10-day old embryonated SPF chicken eggs are inoculated with 100 µl 10-fold serial dilution per egg into the allantoic cavity in 6 replicates per dilution. Infected eggs are incubated for 7 days and candling is conducted every 24 h in order to determine mortality. Eggs with dead embryos prior to 24 hours of incubation are not included in the evaluation. The $EID_{50}$/mL is calculated as described by Reed & Muench.

Determination of the 50% Tissue Culture Infectious Dose ($TCID_{50}$)

For the determination of the $TCID_{50}$, 2.5 to $3*10^5$ cells with a viability of at least 90% are seeded per well into a 96 well plate one day prior to infection with a 10-fold dilution series of passaged IBV Mass. Medium is removed from the cells and they are infected with 100 µl per well in 5 replicates per dilution. After 72 hours of static incubation at 37° C. and 7.5% $CO_2$, medium is removed and cells are fixed for 15 min at 4° C. with 50 µl 80% acetone per well. A washing step with 1×PBS is conducted and followed by incubation with 50 µl per well of a 1:1000 dilution of anti-IBV Mass antiserum (Charles River Laboratories, Cat.: 10100454) at 37° C. for 1 hour. The plates are washed twice with 1×PBS before 50 µl of a 1:2000 dilution of Alexa 488-conjugated anti-chicken antibody (Invitrogen, Cat.: A11039) are added and incubated at 37° C. for 1 hour. Subsequently, a final wash with 1×PBS is conducted and 100 µl of 1×PBS are added into each well followed by the evaluation in an inverted fluorescence microscope. The infectious titer of IBV in EB66® cells is determined according to the formula of Reed & Muench.

Infectivity of IB66HP for Different Cell Lines

Figure 2:
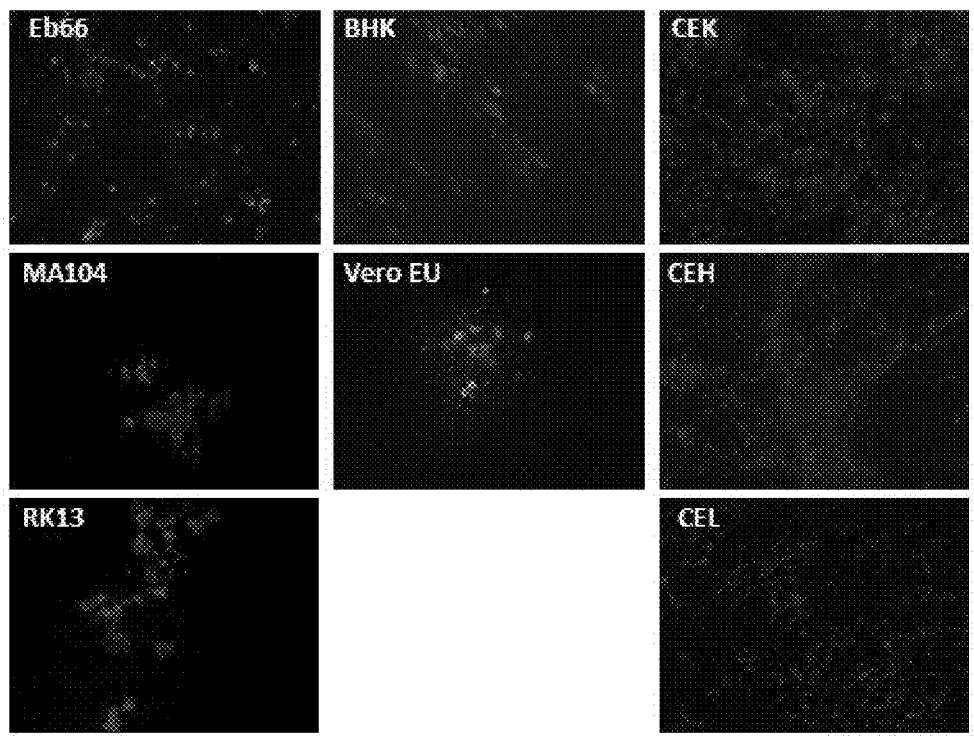
FIG. 2.: Immunofluorescence staining for IB66HP 72 hours after infection of different cell lines. Negative controls were included but are not shown.

Different cell lines are seeded into 96 well plates to reach 70-80% confluence the next day. Cells are infected with a 10-fold dilution series of an IB66HP P8 set to a titer of $10^5$ to $10^{5.75}$ TCID$_{50}$/ml derived from titration on EB66® cells. Medium is removed from the cells and they are infected with 100 µl per well in 4 replicates per dilution. After 72 hours the TCID$_{50}$ titer is determined. Indeed, infectivity of IB66HP for different primary cells and cell lines is detected and results are listed in table 2 and 3 and shown in FIG. 2.

TABLE 2

IB66HP has an extended tissue tropism. TCID$_{50}$ determination in various cell lines for IB66HP set to a titer of $10^5$ TCID$_{50}$ prior to titration.

| Cell | Species | Tissue | Log TCID$_{50}$/ml |
|---|---|---|---|
| EB66 | duck | Embryonic stem cell | 5 |
| BHK | hamster | Kidney | 4 |
| MA104 | African green monkey | Kidney | 2 |
| Vero EU | African green monkey | Kidney | 2.67 |
| RK13 | rabbit | Kidney | 3 |
| CEK | Chicken embryo | Primary kidney | 5.33 |
| CEH | Chicken embryo | Primary liver | 3.67 |
| CEL | Chicken embryo | Primary lung | 6 |

TABLE 3

IB66HP has an extended tissue tropism. TCID$_{50}$ determination in various cell lines for IB66HP set to a titer of $10^{5.75}$ TCID$_{50}$ prior to titration.

| Cell | Species | Tissue | Log TCID$_{50}$/ml |
|---|---|---|---|
| SF9 | Fall armyworm | Pupal ovarian tissue | 5.6 |
| CEF | Chicken embryo | Primary fibroblasts | 4.5 |
| MDCK | Dog | kidney | 5.38 |

Conclusion Example 1

The attenuated IBV M41 was adapted to cell culture. The deposited strain as well as descendants show an extended cell or tissue tropism as they were able to infect in primary cells and a broad range of different cell lines.

Example 2

Determination of IB66HP Safety and Efficacy In Vivo

The attenuated IBV Mass allantoic fluid stock (P0) and passages 5 (P5) and 10 (P10) in EB66® cells are used to assess their safety and efficacy in 1-day-old SPF layer chickens against virulent M41 challenge. Throughout the whole study chickens are housed in isolation units and are provided with water and commercial balanced feed formula ad libitum. Chickens are observed daily for clinical signs. Three groups of chickens are vaccinated with P0, P5 and P10 each, at a dose of $10^4$ TCID$_{50}$/chicken via eye drop. One group is treated with placebo and serves as challenge control group. Seven days post vaccination seven animals per group vaccinated with P0, P5 or P10 are euthanized to assess the safety via scoring of the tracheal ciliostasis. For this, the trachea is removed and cut into transversal sections of which 3 of the lower, 4 of the middle and 3 of the upper part are used for safety assessment. All rings are evaluated by light microscopy for beating of the cilia. Each ring is scored individually as described in table 4.

TABLE 4

Ciliostasis scoring scheme for the assessment of safety

| Score | Ciliar activity [%] |
|---|---|
| 0 | 100 |
| 1 | 75-99 |
| 2 | 50-74 |
| 3 | 25-49 |
| 4 | 0-24 |

Twenty-one days post vaccination all remaining chickens are challenged with virulent IBV M41 with a dose of $10^{2.5}$ EID$_{50}$/chicken via eye drop. Efficacy is assessed at seven days post vaccination by ciliostasis scoring as described in table 4. A ring is recorded as normal if more than 50% of the internal ring shows vigorous ciliar movement (Score 2 and lower). A ring is recorded as positive for ciliostasis if less than 50% of the cilia are beating (Score 3 and 4). An animal is considered protected if not fewer than 9 out of 10 rings show normal ciliar activity. Throughout the whole study, all animals are observed daily for clinical signs such as depression, respiratory, digestive or neurological signs, locomotive damage, prostration or ruffled feathers.

The aim of the study is to determine whether the cell culture adaptation and cell passage of IB66HP has an effect on safety and efficacy compared to the parental IBV M41att allantoic fluid stock when applied to 1-day-old chickens. The assessment of safety by clinical signs and ciliostais scoring of tracheal explants revealed that P5 and P10 of IB66HP in Eb66® cells have an improved safety profile compared to IBV M41att. The ciliostasis score are strongly reduced for IB66HP P5 and P10 in contrast to IBV M41att (table 5). In addition, clinical signs in the animals of groups vaccinated with IB66HP P5 and P10 were reduced compared to the animals vaccinated with M41att. Conclusively, IB66HP is more attenuated than M41att and has an improved safety profile for vaccination of 1-day-old chickens.

TABLE 5

Results for assessment of safety for IB66HP EB66 ® cell passage 5 (P5) and 10 (P10) in comparison to the allantoic fluid stock of M41att 5 days post vaccination. The mean ciliostasis score per group is calculated by adding up the sum score of the individual chickens per group and dividing the group sum by the number of animals (highest possible score 40, lowest possible score 0). For not affected animals, at least 9 of the 10 tracheal explants show normal ciliar activity (score ≤2).

| Vaccination | Mean ciliostasis score | #Animals/not affected |
|---|---|---|
| M41att P0 | 30.6 | 5/1 |
| IB66HP P5 | 8.2 | 5/5 |
| IB66HP P10 | 6.4 | 5/5 |
| — | 0.4 | 5/5 |

All animals of the non-vaccinated control group show clinical signs and a high ciliostasis score after challenge with virulent IBV M41. In contrast, the EB66® cell passaged IB66HP P5 and P10 are able to reduce clinical signs and the damage of the trachea as efficiently as M41att (table 6).

TABLE 6

Results for assessment of efficacy for IB66HP EB66 ®
cell passage 5 (P5) and 10 (P10) in comparison to the allantoic
fluid stock of M41att 7 days post challenge. The mean ciliostasis
score per group is calculated by adding up the sum score of
the individual chickens per group and dividing the group sum
by the number of animals (highest possible score 40, lowest
possible score 0). For not affected animals, at least 9 of
the 10 tracheal explants show normal ciliar activity (score ≤2).

| Vaccination | Challenge | Mean ciliostasis score | #animals/Not affected | % animals with normal ciliostasis |
|---|---|---|---|---|
| M41att P0 | M41 | 2.2 | 7/7 | 100 |
| IB66HP P5 | M41 | 0.1 | 9/9 | 100 |
| IB66HP P10 | M41 | 3 | 10/9 | 90 |
| — | M41 | 35.9 | 9/0 | 0 |

In summary, IB66HP is an attenuated IBV strain that efficiently infects and replicates in different cell lines and tissue cells. Surprisingly, it has an improved safety for application in 1-day-old chickens compared to the parental egg-restricted IBV M41att strain. Furthermore, IB66HP maintains vaccine efficacy. In contrast, the only other known cell culture adapted and highly attenuated IBV strain Beaudette does not confer sufficient protection after challenge infection. Thus, IB66HP is the first described IBV that is attenuated, has an extended cell culture or tissue tropism and displays efficacy against virulent challenge after application as a vaccine. Further, IB66HP has been shown to be phenotypically stable.

The invention claimed is:

1. An infectious bronchitis virus (IBV) deposited with the Biobank of Veterinary Resources (BVR) of the Istituto Zooprofilattico Sperimentale della Lombardia e dell'Emilia Romagna (IZSLER) under accession number DPS RE RSCIC 16, or any descendant IBV thereof obtained by passaging from the deposited IBV.

2. The IBV of claim 1, wherein the IBV is attenuated.

3. The IBV of claim 1, wherein the IBV is non-recombinant.

4. The IBV of claim 1, wherein the IBV is of a Massachusetts genotype or serotype.

5. The IBV of claim 1, wherein the IBV has an extended cell or tissue tropism.

6. The IBV of claim 1, wherein the IBV is capable of infecting and/or replicating in a cell line or cell selected from the list consisting of: primary chicken embryo cells from lung or liver or primary chicken fibroblasts, a chicken embryo fibroblast cell line, a duck embryonic stem cell line, a human embryonic kidney cell line, a baby hamster kidney cell line, an African green monkey kidney cell line, a rabbit kidney cell line, a canine kidney cell line, a chicken liver cell line, a bovine kidney cell line, a porcine kidney cell line and an insect cell line.

7. The IBV of claim 1, wherein the IBV is capable of infecting and/or replicating in at least one cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A, SF9, SF21 and SF+ (*Spodoptera frugiperda*).

8. The IBV of claim 1, wherein the attenuation of the IBV is increased compared to an IBV without extended cell or tissue tropism.

9. A plasmid comprising a nucleotide sequence encoding the IBV of claim 1.

10. A cell comprising the IBV of claim 1.

11. An immunogenic composition comprising the IBV of claim 1.

12. The immunogenic composition of claim 11, wherein the immunogenic composition is a vaccine.

13. The immunogenic composition of claim 11, wherein the immunogenic composition is a modified live vaccine.

14. A method for immunizing a subject comprising administering to such subject the immunogenic composition of claim 11.

15. A method of treating or preventing clinical signs caused by IBV in a subject of need, the method comprising administering to the subject a therapeutically effective amount of the immunogenic composition of claim 11.

16. A method of reducing the ciliostasis in a subject of need, in comparison to a subject of a non-immunized control group of the same species, the method comprising administering to the subject a therapeutically effective amount of the immunogenic composition of claim 11.

17. The method of claim 14, wherein the subject is chicken.

18. The method of claim 14, wherein the immunogenic composition is administered once.

19. The method of claim 14, wherein the immunogenic composition is administered subcutaneously, intramuscularly, orally, in ovo, via spray, via drinking water or by eye drop.

20. A cell comprising the plasmid of claim 9.

* * * * *